US011633105B2

(12) United States Patent
Zhang et al.

(10) Patent No.: US 11,633,105 B2
(45) Date of Patent: Apr. 25, 2023

(54) IMAGE PROCESSING SYSTEM, FLUORESCENT ENDOSCOPIC ILLUMINATED IMAGING APPARATUS AND IMAGING METHOD

(71) Applicant: Shanghai Kinetic Medical Co., Ltd, Shanghai (CN)

(72) Inventors: Shengjin Zhang, Shanghai (CN); Wei Tang, Shanghai (CN)

(73) Assignee: SHANGHAI KINETIC MEDICAL CO., LTD, Shanghai (CN)

( * ) Notice: Subject to any disclaimer, the term of this patent is extended or adjusted under 35 U.S.C. 154(b) by 324 days.

(21) Appl. No.: 17/044,766

(22) PCT Filed: Aug. 20, 2018

(86) PCT No.: PCT/CN2018/101378
§ 371 (c)(1),
(2) Date: Oct. 1, 2020

(87) PCT Pub. No.: WO2019/205359
PCT Pub. Date: Oct. 31, 2019

(65) Prior Publication Data
US 2021/0106214 A1    Apr. 15, 2021

(30) Foreign Application Priority Data
Apr. 25, 2018    (CN) .......................... 201810376241.4

(51) Int. Cl.
*A61B 5/00*       (2006.01)
*A61B 1/00*       (2006.01)
(Continued)

(52) U.S. Cl.
CPC ........ *A61B 5/0071* (2013.01); *A61B 1/00009* (2013.01); *A61B 1/00096* (2013.01);
(Continued)

(58) Field of Classification Search
CPC . A61B 1/00009; A61B 1/00096; A61B 1/043; A61B 1/045; A61B 1/046; A61B 1/0638; A61B 1/0646
See application file for complete search history.

(56) References Cited

U.S. PATENT DOCUMENTS 9,763,299 B1* 9/2017 Liang ..................... H05B 45/10
2010/0245616 A1* 9/2010 Yoshino ............... G01N 21/645
382/163
(Continued)

FOREIGN PATENT DOCUMENTS

CN    101584572 A    11/2009
CN    102781305 A    11/2012
(Continued)

*Primary Examiner* — Aaron B Fairchild
*Assistant Examiner* — Julianna J Nicolaus
(74) *Attorney, Agent, or Firm* — Muncy, Geissler, Olds & Lowe, P.C.

(57) ABSTRACT

An imaging method of a fluorescent image performs image processing before generating colored-fluorescent images, including steps: respectively imaging the red, green and blue lights of the white light on three monochromatic sensors under the precondition that the software processing speed is not affected; imaging the near infrared fluorescent light on one of the monochromatic sensors; determining whether the sensor used to receive the near infrared fluorescent light receives the fluorescent signal; calculating the light intensity received by the sensor receiving the fluorescent signal and the light intensities received by the other two sensors; automatically adjusting the projection intensity of the white light source and/or the excitation light source according to the difference of the intensities of the two types of light signals, whereby a closed-loop system is formed to simultaneously present the colored-florescent images on a picture with the best contrast.

16 Claims, 9 Drawing Sheets

(51) Int. Cl.
*A61B 1/04* (2006.01)
*A61B 1/05* (2006.01)
*A61B 1/06* (2006.01)

(52) U.S. Cl.
CPC .......... *A61B 1/00126* (2013.01); *A61B 1/043* (2013.01); *A61B 1/05* (2013.01); *A61B 1/0646* (2013.01); *A61B 1/0653* (2013.01); *A61B 1/0655* (2022.02); *A61B 1/0661* (2013.01)

(56) References Cited

U.S. PATENT DOCUMENTS

2014/0187879 A1    7/2014  Wood et al.
2016/0062103 A1*  3/2016  Yang ........................ A61B 1/07
                                                            250/552
2016/0287081 A1*  10/2016  Yang .................... A61B 5/0071
2017/0035280 A1*  2/2017  Yang ...................... A61B 1/043
2017/0289467 A1*  10/2017  Yamamoto ......... H04N 9/04553

FOREIGN PATENT DOCUMENTS

| CN | 104274156 A | | 1/2015 |
|---|---|---|---|
| CN | 105263390 A | | 1/2016 |
| CN | 105764401 A | | 7/2016 |
| CN | 106236006 A | * | 12/2016 |
| CN | 107072520 A | | 8/2017 |
| CN | 107635451 A | | 1/2018 |
| CN | 108095701 A | | 6/2018 |

* cited by examiner

IMAGE PROCESSING SYSTEM, FLUORESCENT ENDOSCOPIC ILLUMINATED IMAGING APPARATUS AND IMAGING METHOD

BACKGROUND OF THE INVENTION

Field of the Invention

The present invention relates to an imaging technology of an endoscope, particularly to an image processing system, a fluorescent endoscope illuminating and imaging device, and an imaging method thereof.

Description of the Related Art

With the development of molecular imaging technology, the advantage of the fluorescent endoscopy becomes more and more obvious in detecting microscopic molecular activity, such as variation and metastasis of cancer. For example, near infrared fluorescence has been widely used in detecting the clinical labels of the sentinel lymph nodes of breast cancer, thyroid cancer, cervical cancer, and intestinal cancer. In operation, an indocyanine green (ICG) agent is injected into the body of a patient; later, a near infrared excitation light and a white light are turned on to illuminate the inspected region of the patient; the excitation light projects onto the abnormal tissue having combined with the ICG agent to make the molecules emit near infrared fluorescence, and the normal tissue reflects the white light; the imaging system of the endoscope absorbs the near infrared fluorescence and the white light and performs photoelectric conversion and image processing to present colored-fluorescent synthesis image on a terminal display; then, the image is analyzed to obtain the pathological variation of the corresponding tissue.

The definition of the colored-fluorescent synthesis image is critical for accurately analyzing the pathological variation of the corresponding tissue. In order to guarantee the definition of the colored-fluorescent synthesis image, the colored image and the fluorescent image need to be output in a picture in the best contrast.

In order to output the colored image and the fluorescent image of a picture in the best contrast, the existing method normally respectively generates a colored image and a fluorescent image and then uses software to adjust the brightness and contrast of the images, whereby to output a colored-fluorescent image with the best contrast. The practical process includes steps:

S1: respectively using different sensors to receive the reflected illumination light for acquiring a colored image and receive the fluorescent light excited by the excitation light for acquiring a fluorescent image;

S2: performing a subtraction or division processing of the colored image and the fluorescent image, which are acquired in the preceding step, to extract a new fluorescent image that belongs to the lesion region only;

S3: synthesizing the colored image and the new fluorescent image, and modifying the brightness and the contrast thereof to the best state;

S4: outputting a modified colored-fluorescent image.

The abovementioned existing method has the following disadvantages: the method is too complicated; the precision thereof is insufficient; the output of the synthesized image is delayed by an image, and the viewers feel the presentation of images is delayed; mismatch between two successively acquired images will affect the completeness of the fluorescent image.

Therefore, it has been a target that the manufacturers are eager to achieve: how to simply and precisely process images to acquire colored-fluorescent images having or almost having the best contrast.

SUMMARY OF THE INVENTION

One objective of the present invention is to provide an imaging method of a fluorescent image, which processes images before generating a colored-fluorescent image, whereby to generate a colored-fluorescent image having or almost having the best contrast.

Another objective of the present invention is to provide an image processing system, which can process images in a simple way before generating a colored-fluorescent image.

Yet another objective of the present invention is to provide a fluorescent endoscope illuminating and imaging device, which can process images before generating a colored-fluorescent image, whereby to generate a colored-fluorescent image having or almost having the best contrast.

In order to achieve the abovementioned objectives, the present invention proposes an imaging method of a fluorescent image, which comprises steps:

S1: using a white light source and an excitation light source to illuminate an inspected area, wherein the excitation light source is adjusted to have the highest intensity; respectively imaging the red light, green light and blue light of a reflection of a white light on a red light sensor, a green light sensor and a blue light sensor; using one of the red light sensor, the green light sensor and the blue light sensor to image the near infrared fluorescent light emitted from the inspected area;

S2: making weighted average of the intensities of the light signals of two of the red, green and blue lights, which are received by each pixel of the two sensors not receiving the near infrared fluorescent light, to obtain an intensity value (denoted by a0) of a third light signal;

S3: determining in sequence whether the light intensity a1 received by each pixel of the sensor imaging the near infrared fluorescent light is greater than the intensity value a0 generated in the step S2; if yes, the process proceeding to a step S4; if no, the process proceeding to a step S8;

S4: determining whether successive N pixels all satisfy a1>a0; if yes, the process proceeding to a step S5; if no, lowering the intensity of the white light source, and the process returning to the step S2, wherein N is a natural number and N≥2; S5: controlling the sensor, which images the near infrared fluorescent light, to output near infrared fluorescent light signals, and controlling the other two sensors not to output signals; acquiring the average intensity (denoted by a1') of the near infrared fluorescent light signals within a given area of the corresponding sensor;

S6: determining whether the difference between a1' and a0 achieves or approaches a predetermined best value; if yes, the process proceeding to a step S7; if no, adjusting the intensity of the white light source, and the process returning to the step S2;

S7: outputting the video signals of the near infrared fluorescent light;

S8: determining whether a1<a0; if yes, decreasing the intensity of the white light source, and the process returning to the step S2; if no, the process proceeding to a step S9;

S9: decreasing the intensity of the white light source;

S10: determining in sequence whether the light intensity a11 received by each pixel of the sensor that images the near infrared fluorescent light is smaller than the light intensity a0 acquired in the step S2 after the intensity of the white light source is decreased; if no, the process returning to the step S2; if yes, the process proceeding to a step S11;

S11: restoring the intensity of the white light source to the value appearing before the intensity of the white light source is decreased;

S12: outputting RGB colored video signals;

S13: outputting colored-fluorescent video signals according to the near infrared fluorescent video signals output in the step S7 and the RGB colored video signals output in the step S12.

In one embodiment, a step S20 is interposed between the step S1 and the step S2.

S20: determining whether the excitation light source is turned on and has reached the maximum intensity; if yes, the process proceeding to the step S2; if no, adjusting the excitation light source and determining whether the excitation light source has reached the maximum intensity.

The present invention also proposes another imaging method of a fluorescent image, which comprises steps:

S1: using a white light source and an excitation light source to illuminate an inspected area, wherein the excitation light source is adjusted to have the highest intensity; respectively imaging the red light, green light and blue light of a reflection of a white light on a red light sensor, a green light sensor and a blue light sensor; using one of the red light sensor, the green light sensor and the blue light sensor to image the near infrared fluorescent light emitted from the inspected area;

S2: making weighted average of the intensities of the light signals of two of the red, green and blue lights, which are received by each pixel of the two sensors not receiving the near infrared fluorescent light, to obtain an intensity value (denoted by a0) of a third light signal;

S3: determining in sequence whether the light intensity a1 received by each pixel of the sensor imaging the near infrared fluorescent light is greater than the intensity value a0 generated in step S2; if yes, the process proceeding to a step S4; if not, the process proceeding to a step S7;

S4: determining whether successive N pixels all satisfy a1>a0; if yes, the process proceeding to a step S5; if no, lowering the intensity of the white light source, and the process returning to the step S2, wherein N is a natural number and N≥2;

S5: controlling the sensor, which images the near infrared fluorescent light, to output near infrared fluorescent light signals, and controlling the other two sensors not to output signals; determining whether the contrast of the near infrared fluorescent light signal and the RGB background light achieves or approaches a predetermined best value; if yes, the process proceeding to a step S6; if no, adjusting the intensity of the white light source, and the process returning to the step S2;

S6: outputting the video signals of the near infrared fluorescent light;

S7: determining whether the reason why a1 is not greater than a0 is that the inspected area does not emit near infrared fluorescent light; if yes, the process proceeding to a step S8; if no, decreasing the intensity of the white light source, and the process returning to the step S2;

S8: outputting RGB colored video signals;

S9: outputting colored-fluorescent video signals according to the near infrared fluorescent video signals output in the step S6 and the RGB colored video signals output in the step S8.

In one embodiment, the step of determining whether the contrast of the near infrared fluorescent light signal and the RGB background light achieves or approaches the predetermined best value in the step S5 further includes steps:

S51: acquiring the average intensity (denoted by a1') of the near infrared fluorescent light signals within a given area of the corresponding sensor;

S52: determining whether the difference between a1' and a0 achieves or approaches the predetermined best value; if yes, determining that the contrast of the near infrared fluorescent light signal and the RGB background light achieves or approaches the predetermined best value; if no, determining that the contrast of the near infrared fluorescent light signal and the RGB background light does not achieve or approach the predetermined best value.

In one embodiment, the step S7 further includes steps:

S71: determining whether a1<a0; if yes, decreasing the intensity of the white light source, and the process returning to the step S2; if no, decreasing the intensity of the white light source, and the process proceeding to a step S72;

S72: determining in sequence whether the light intensity a11 received by each pixel of the sensor that images the near infrared fluorescent light is smaller than the light intensity a0 acquired in the step S2 after the intensity of the white light source is decreased; if no, the process returning to the step S2; if yes, the process proceeding to a step S73;

S73: restoring the intensity of the white light source to the value appearing before the intensity of the white light source is decreased;

S74: the red light sensor, the green light sensor and the blue light sensor respectively outputting their light signals.

In one embodiment, a step S20 is interposed between step S1 and step S2.

S20: determining whether the excitation light source is turned on and has reached the maximum intensity; if yes, the process proceeding to the step S2; if no, adjusting the excitation light source and determining whether the excitation light source has reached the maximum intensity.

The present invention further proposes yet another imaging method of a fluorescent image, which comprises steps:

S1: using a white light source and an excitation light source to illuminate an inspected area; respectively imaging the red light, green light and blue light of a reflection of a white light on a red light sensor, a green light sensor and a blue light sensor; using one of the red light sensor, the green light sensor and the blue light sensor to image the near infrared fluorescent light emitted from the inspected area;

S2: determining whether the sensor, which images the near infrared fluorescent light, receives near infrared fluorescent light signals; if yes, the process proceeding to a step S3; if no, the process proceeding to a step S6;

S3: determining whether the near infrared fluorescent light signals are received by N successive pixels; if yes, the process proceeding to a step S4; if no, decreasing the intensity of the white light source, and the process returning to the step S2, wherein N is a natural number and N≥2;

S4: controlling the sensor, which images the near infrared fluorescent light, to output near infrared fluorescent light signals, and controlling the other two sensors not to output signals; determining whether the contrast of the near infrared fluorescent light signal and the RGB background light achieves or approaches a predetermined best value; if yes, the process proceeding to a step S5; if no, adjusting the intensity of the white light source, or adjusting the intensity of the excitation light source, or adjusting the intensity of the white light source and the intensity of the excitation light source at the same time, and the process returning to the step S2;

S5: outputting the video signals of the near infrared fluorescent light;

S6: determining whether the reason why the near infrared fluorescent light signals are not received in the step S2 is indeed that the inspected area does not emit near infrared fluorescent light; if yes, the process proceeding to a step S7; if no, decreasing the intensity of the white light source, and the process returning to the step S2;

S7: outputting RGB colored video signals;

S8: outputting colored-fluorescent video signals according to the near infrared fluorescent video signals output in the step S5 and the RGB colored video signals output in the step S7.

In one embodiment, the step S2 includes steps:

S21: making weighted average of the intensities of the light signals of two of the red, green and blue lights, which are received by each pixel of the two sensors not receiving the near infrared fluorescent light, to obtain an intensity value (denoted by a0) of a third light signal;

S22: determining in sequence whether the light intensity a1 received by each pixel of the sensor imaging the near infrared fluorescent light is greater than the intensity value a0 generated in the step S21; if yes, determining that the sensor, which images the near infrared fluorescent light, receives near infrared fluorescent signals; if no, determining that the sensor, which images the near infrared fluorescent light, does not receive near infrared fluorescent signals.

In one embodiment, the step of determining whether the contrast of the near infrared fluorescent light signal and the RGB background light achieves or approaches the predetermined best value in the step S4 further includes steps:

S41: acquiring the average intensity (denoted by a1') of the near infrared fluorescent light signals within a given area;

S42: determining whether the difference between a1' and a0 achieves or approaches the predetermined best value; if yes, determining that the contrast of the near infrared fluorescent light signal and the RGB background light achieves or approaches the predetermined best value; if no, determining that the contrast of the near infrared fluorescent light signal and the RGB background light does not achieve or approach the predetermined best value.

In one embodiment, the step S6 includes steps:

S61: determining whether a1 is smaller than a0; if yes, decreasing the intensity of the white light source, and the process returning to the Step S2; if no, decreasing the intensity of the white light source, and the process proceeding to a step S62;

S62: determining in sequence whether the light intensity a11 received by each pixel of the sensor that images the near infrared fluorescent light is smaller than the light intensity a0 acquired in the step S21 after the intensity of the white light source is decreased; if no, the process returning to the step S2; if yes, the process proceeding to a step S63;

S63: restoring the intensity of the white light source to the value appearing before the intensity of the white light source is decreased;

S64: the red light sensor, the green light sensor and the blue light sensor respectively outputting their light signals;

S65: outputting RGB colored video signals according to the light signals output by the red light sensor, the green light sensor and the blue light sensor.

In one embodiment, adjusting the intensity of the excitation light source in the step S4 is to adjust the intensity of the excitation light source to the maximum value.

The present invention also proposes an image processing system, which comprises a pulse generator and an image processor. The image processor further comprises a signal conversion unit, a signal processing unit, a comparison unit, an instruction unit, and a signal output unit.

The signal conversion unit respectively picks up the intensity values of the light signals received by each pixel of the red light sensor, the green light sensor and the blue light sensor and undertakes the photoelectric conversions of the light signals. The red light sensor, the green light sensor and the blue light sensor respectively image the red light, the green light and the blue light of a reflection of a white light. One of the red light sensor, the green light sensor and the blue light sensor images the near infrared fluorescent light. The reflection of the white light is reflected from an inspected area illuminated by a white light source. The near infrared fluorescent light is emitted from the inspected area illuminated by an excitation light source.

After the photoelectric-conversion, the signal processing unit makes weighted average of the intensity values of the light signals of two of the red, green and blue lights, which are received by each pixel of the two sensors not receiving the near infrared fluorescent light, to obtain an intensity value (denoted by a0) of a third light signal.

The comparison unit compares an intensity value a1 with the intensity value a0, wherein a photoelectric conversion of the light signals received by each pixel of the sensor receiving the near infrared fluorescent light signal is undertaken to obtain the intensity value a1.

The instruction unit receives the comparison result from the comparison unit to make determinations and perform corresponding operations.

In the case that a1>a0, if N successive pixels all satisfy a1>a0, the instruction unit sends out a first instruction to the pulse generator; the pulse generator controls the sensor, which receives the near infrared fluorescent light, to output the near infrared fluorescent signals and controls the other two sensors not to output light signals. Let a1' be the average value of the intensities of the near infrared fluorescent light signals within a given area of the sensor receiving the near infrared fluorescent light. If the difference between a1' and a0 achieves or approaches a predetermined best value, the instruction unit sends out a second instruction. If the difference between a1' and a0 does not achieve or approach the predetermined best value, the instruction unit sends out a third instruction to decrease the intensity of the white light source.

In the case that a1>a0, if N successive pixels do not all satisfy a1>a0, the instruction unit sends out the third instruction to decrease the intensity of the white light source. If the difference between a1' and a0 does not achieve or approach the predetermined best value, the instruction unit sends out a fourth instruction to increase or decrease the intensity of the white light source.

In the case that a1<a0, the instruction unit sends out the third instruction to decrease the intensity of the white light source.

In the case that a1=a0, the instruction unit sends out the third instruction to decrease the intensity of the white light source, and compare an intensity value a11 with the intensity value a0, wherein the photoelectric conversion of the light signal received by each pixel of the sensor that receives the near infrared fluorescent light is undertaken after decreasing the intensity of the white light source to obtain the intensity value a11. If a11<a0, the instruction unit sends out a fifth instruction to restore the intensity of the white light source to the value appearing before the intensity of the white light is decreased, and sends out the second instruction to the pulse generator to control the red, green and blue sensors to respectively output the red, green and blue light signals under the condition that the intensity of the white light source has been restored.

The signal output unit receives the second instruction and outputs the colored-fluorescent video signals according to the near infrared fluorescent signal output by the near infrared fluorescent light sensor and the red, green and blue light signals output by the red light, green light and blue light sensors.

The present invention also proposes a fluorescent endoscope illuminating and imaging device, which comprises the abovementioned image processing system.

In one embodiment, the fluorescent endoscope illuminating and imaging device of the present invention further comprises a light projection device, an optical pickup member, an image pickup member, and an image display member.

The light projection device provides a white light and an excitation light whose intensities are adjustable to illuminate an inspected area.

The optical pickup member transmits and couples the white light reflected from the inspected area and the near infrared fluorescent light emitted from the inspected area to the image pickup member.

The image pickup member includes a light-splitting prism group, a red light sensor, a green light sensor and a blue light sensor. The light-splitting prism group splits the white light, which is reflected from the inspected area and coupled to the image pickup member, into an R light, a G light, and a B light, and respectively images the R, G and B lights on the red light sensor, the green light sensor and the blue light sensor. The near infrared fluorescent light, which is coupled to the image pickup member and passes through the light-splitting prism group, is imaged on one of the red light sensor, the green light sensor and the blue light sensor.

The image display member undertakes signal conversion of the colored-fluorescent video signals output by the image processing system and outputs colored-fluorescent images.

In one embodiment, the light projection device includes a white light source, an excitation light source and a light source control member. The light source control member modifies the intensities of the white light source and the excitation light source.

In one embodiment, the optical pickup member includes an imaging lens group and an optical adapter. The optical adapter is disposed at the rear end of the imaging lens group. The imaging lens group transmits the white light reflected from the inspected area and the near infrared fluorescent light emitted from the inspected area. The optical adapter couples the reflection of the white light and the emitted near infrared fluorescent light to the image pickup member.

In one embodiment, the optical adapter includes light filters. The light filters screen out the excitation light from the inspected area and allows the reflection of the white light and the emitted near infrared fluorescent light to pass.

In one embodiment, the imaging lens group is a portion of the endoscope.

Based on the abovementioned technical schemes, the present invention has the following advantages outperforming the existing technologies:

1) The imaging method of a fluorescent image of the present invention performs image processing before generating the colored-fluorescent images, including steps: respectively imaging the red, green and blue lights of the white light on three monochromatic sensors under the precondition that the software processing speed is not affected; imaging the near infrared fluorescent light on one of the monochromatic sensors; determining whether the sensor used to receive the near infrared fluorescent light receives the fluorescent signals; calculating the light intensity received by the sensor receiving the fluorescent signals and the light intensities received by the other two sensors; automatically adjusting the projection intensity of the white light source and/or the excitation light source according to the difference of the intensities of the two types of light signals, whereby a closed-loop system is formed to simultaneously present the colored-florescent images on a picture with the best contrast. The method of the present invention can automatically adjust the intensities of the white light and the excitation light to maintain a given difference between the fluorescent light signal and the background colored light signal. Therefore, the method of the present invention can precisely and conveniently determine whether the fluorescent light signal exists. While the fluorescent light signal exists, the method of the present invention guarantees that the brightness of the colored background is sufficient to allow physicians to observe the body cavity conveniently and precisely.

2) Because of performing image processing before imaging, the method of the present invention handles smaller volume of data, computes faster, and output pictures smoothly.

DETAILED DESCRIPTION OF THE INVENTION

Below, embodiments and attached drawings are used to further demonstrate the image processing system, the fluorescent endoscope illuminating and imaging device, and the imaging method of the present invention. The demonstration and claims stated below will make clear the characteristics and advantages of the present invention. It should be explained: the attached drawings are not drawn in an accurate proportion but depicted in a simplified form so as to explain the embodiments clearly and conveniently. It should be understood by the persons skilled in the art: although the specification and claims use some terminologies to name some specified elements, the manufacturers may use other terms to name the same elements. In the specification and claims, different elements are not discriminated by their terms but by their functionalities. In the specification and claims, "comprise" and "include" are "open" terms and should be explained as "the subject contains the objects, but is not limited to only contain the objects". In the specification and claims, "couple" and "connect" refer to any direct or indirect electrical or structural joining. Hence, if the sentence "a first device is coupled to/connected with a second device" appears in the specification or claims, it means that the first device is electrically or structurally joined with the second device directly or that the first device is electrically or structurally joined with the second device indirectly through another device or through a joining means.

Figure 1:
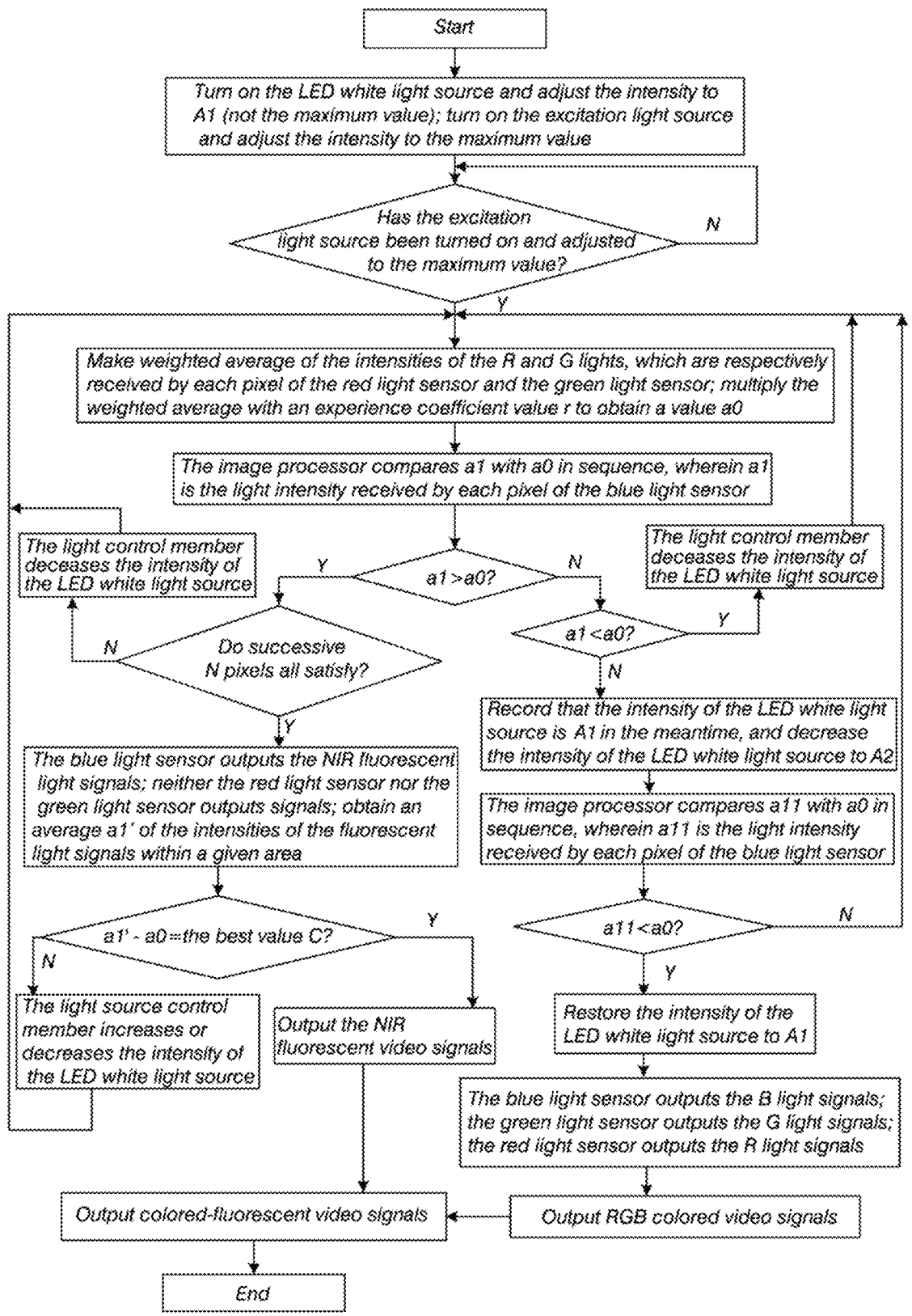
FIG. 1 is a flowchart schematically showing an imaging method of a fluorescent image according to one embodiment of the present invention.

Refer to FIG. 1. In one embodiment, the present invention proposes an imaging method of a fluorescent image, which comprises the following steps.

S1: use a white light source and an excitation light source to illuminate an inspected area, wherein the excitation light source is adjusted to have the highest intensity, and the white light source may have an arbitrary intensity; respectively image the red, green and blue lights of the reflection of the white light on a red light sensor, a green light sensor and a blue light sensor; use the blue light sensor to image the near infrared fluorescent light emitted from the inspected area.

The white light source may be a white LED light source or a light source synthesized with red, green and blue LED light sources. The excitation light source may be an 808±10 nm laser device used to excite the indocyanine green (ICG) agent of the inspected area to generate a near infrared fluorescent light for imaging. However, the present invention is not limited by the abovementioned embodiment or examples. In another embodiment, a red light sensor or a green light sensor is used to image the near infrared fluorescent light emitted from the inspected area.

S20: determine whether the excitation light source is turned on to have a highest intensity; if yes, the process proceeds to a step S2; if no, adjust the excitation light source and determine whether the excitation light source have reached the highest intensity.

The step S20 is preferred in this embodiment. However, the step S20 may be omitted in other embodiments.

S2: make weighted average of the intensities of the red light signals and the green light signals, which are received by each pixel of the red light sensor and the green light sensor, and multiply the weighted average by an experience coefficient r to obtain an intensity value (denoted by a0) of the blue light signal.

S3: determine in sequence whether an intensity a1 received by each pixel of the blue light sensor is greater than a0; if yes, the process proceeds to a step S4; if no, the process proceeds to a step S8.

The case that a1 is greater than a0 indicates that the blue light sensor receives the near infrared fluorescent light signal.

S4: determine whether N successive pixels of the blue light sensor all satisfy a1>a0; if yes, the process proceeds to a step S5; if no, decrease the intensity of the white light source, and the process returns to the step S2; wherein N is a natural number and N≥2.

The step S4 is to exclude false fluorescent signals. The phenomenon that a fluorescent light signal appears in a certain pixel does not necessarily mean that the inspected area indeed emits near infrared fluorescent signals. The fluorescent light signal appearing in a certain pixel may be a false fluorescent light signal. It is hard to confirm that the inspected area indeed emits near infrared fluorescent signals unless fluorescent light signals appear in successive pixels. Via the step S4, the present invention excludes false light signals and thus increases the accuracy of image processing.

S5: control the blue light sensor to output near infrared fluorescent signals, and assign a B color to the near infrared fluorescent signals; control the other two sensors not to output signals; obtain the average of the intensities of the fluorescent signals, and denote the average of the intensities as a1'.

In other embodiments, other colors may be used to represent the near infrared fluorescent signals. In other embodiments, the intensities of the near infrared fluorescent signals within a given area of the blue light sensor are averaged to obtain the average intensity of the near infrared fluorescent signals, and the average is also denoted as a1'.

S6: determine whether the difference between a1' and a0 achieves or approaches a predetermined best value C; if yes, the process proceeds to a step S7; if no, adjust the intensity of the white light source, and the process returns to the step S2.

The best value C is a predetermined value. While the difference between a1' and a0 achieves or approaches the predetermined best value C, the contrast of the fluorescent light and the colored background light achieves or approaches the best state. Thereby, the fluorescent images can be clearly viewed in the colored-fluorescent images synthesized later.

S7: output the B-colored near infrared fluorescent signals.

If another color is assigned to the near infrared fluorescent light signal in the step S5, another color representing the near infrared fluorescent signal would be output in the step S7.

S8: determine whether a1 is smaller than a0; if yes, decrease the intensity of the white light source, and the process returns to the step S2; if no, the process proceeds to a step S9.

S9: decrease the intensity of the white light source.

In details, while it is determined that a1 is not smaller than a0, i.e. a1=a0, the intensity of the white light source at this moment in time is denoted as A1, and the intensity of the white light source is decreased to A2. The phenomenon that a1=a0 indicates that the intensity of the blue light signal, which is converted from the intensities of the red and green light signals received by each pixel of the red and green light sensors, is equal to the intensity of the blue light signal received by the blue light sensor. It is normally determined in such a case that the inspected area does not emit near infrared fluorescent light signals. In other words, the inspected area is a normal tissue. In such a case, the following condition may exist: the average of the intensities of the near infrared fluorescent signals received by the blue light sensor happens to be equal to the intensity of the blue light signal, which is converted from the red and green light sensors. In other words, the intensity of the light signal emitted by an abnormal area is equal to the intensity of the light signal emitted by a normal area. In order to exclude the abovementioned possibility and further increase the accuracy of image processing, the present invention provides a step S10 and a step S11.

S10: determine in sequence whether the light intensity a11 received by each pixel of the blue light sensor after the intensity of the white light source is decreased is smaller than a0; if no, the process returns to the step S2; if yes, the process proceeds to a step s11.

S11: restore the intensity of the white light source to the value appearing before the intensity is decreased, i.e. to A1.

S12: output RGB colored video signals.

In details, the blue light sensor outputs the B light signal; the green light sensor outputs the G light signal; the red light sensor output the R light signal. The RGB colored video signals are output according to the B light signal, the G light signal and the R light signal.

S13: output colored-fluorescent video signals according to the near infrared fluorescent video signals output in the step S7 and the RGB colored video signals output in the step S12.

In details, the colored-fluorescent video signals are presented in an image display member.

Figure 2:
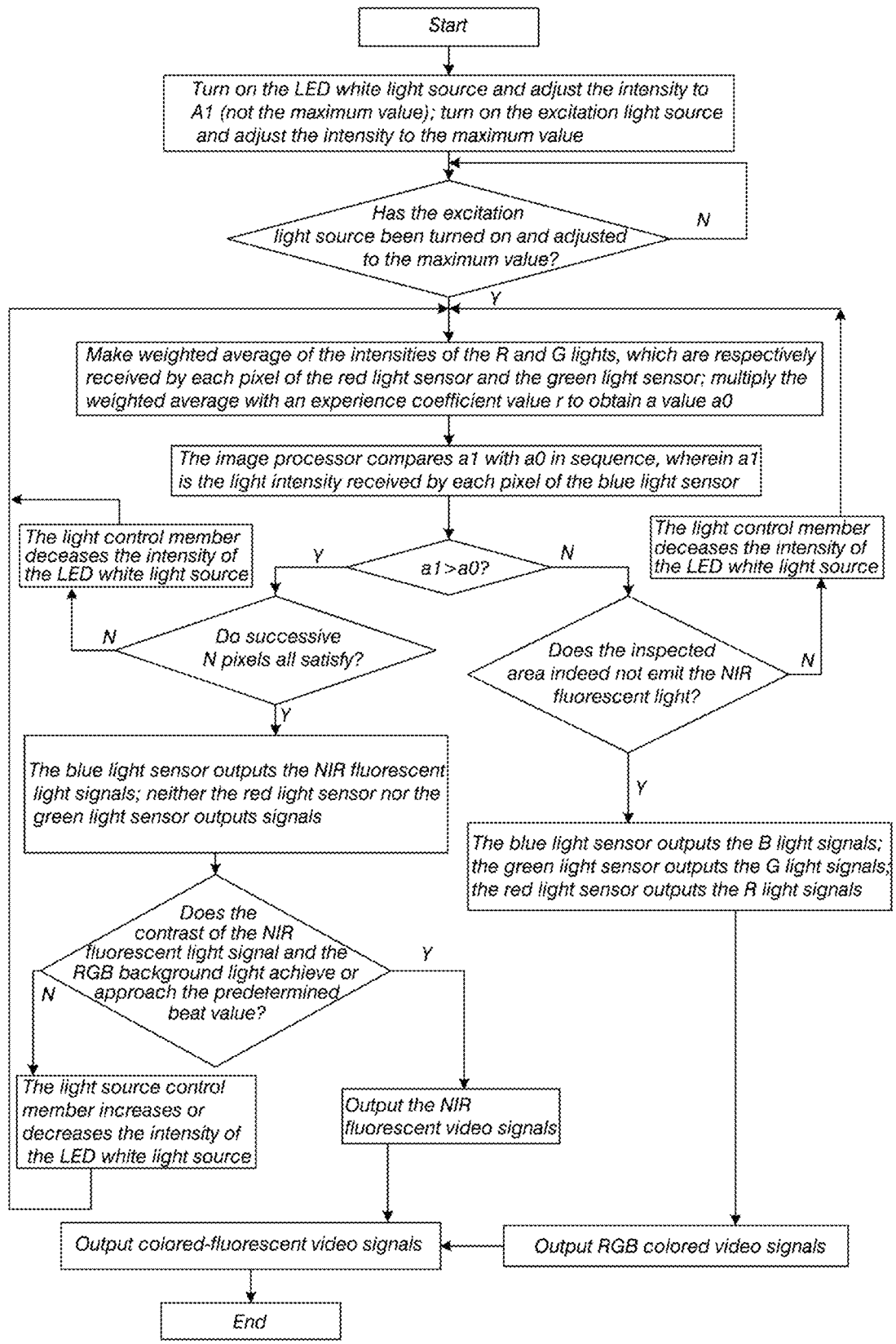
FIG. 2 is a flowchart schematically showing an imaging method of a fluorescent image according to another embodiment of the present invention.

Refer to FIG. 2. In another embodiment, the present invention also proposes an imaging method of a fluorescent image, which comprises the following steps.

S1: use a white light source and an excitation light source to illuminate an inspected area, wherein the excitation light source is adjusted to have the highest intensity, and the white light source may have an arbitrary intensity; respectively image the red light, green light and blue light of the reflection of the white light on a red light sensor, a green light sensor and a blue light sensor; use the blue light sensor to image the near infrared fluorescent light emitted from the inspected area.

The white light source may be a white LED light source or a light source synthesized with red, green and blue LED light sources. The excitation light source may be an 808±10 nm laser device used to excite the indocyanine green (ICG) agent of the inspected area to generate a near infrared fluorescent light. In this embodiment, the blue light sensor is used to image the near infrared fluorescent light emitted from the inspected area. However, it should be understood: the present invention is not limited by this embodiment. In another embodiment, a red light sensor or a green light sensor may be used to image the near infrared fluorescent light emitted from the inspected area.

S2: make weighted average of the intensities of the red light signals and the green light signals, which are received by each pixel of the red light sensor and the green light sensor, and multiply the weighted average by an experience coefficient r to obtain an intensity value (denoted by a0) of the blue light signal.

S3: determine in sequence whether an intensity a1 received by each pixel of the blue light sensor is greater than a0; if yes, the process proceeds to a step S4; if no, the process proceeds to a step S7.

The case that a1 is greater than a0 indicates that the blue light sensor receives the near infrared fluorescent light signal.

S4: determine whether N successive pixels of the blue light sensor all satisfy a1>a0; if yes, the process proceeds to a step S5; if no, decrease the intensity of the white light source, and the process returns to the step S2; wherein N is a natural number and N≥2.

The step S4 is to exclude false fluorescent signals. The phenomenon that a fluorescent light signal appears in a certain pixel does not necessarily mean that the inspected area indeed emits near infrared fluorescent signals. The fluorescent light signal appearing in a certain pixel may be a false fluorescent light signal. It is hard to confirm that the inspected area indeed emits near infrared fluorescent signals unless fluorescent light signals appear in successive pixels. Via the step S4, the present invention excludes false light signals and thus increases the accuracy of image processing.

S5: control the blue light sensor to output near infrared fluorescent signals, and assign a B color to the near infrared fluorescent signals; control the other two sensors not to output signals; determine whether the contrast of the near infrared fluorescent signal and the RGB background light achieves or approaches a predetermined best value; if yes, the process proceeds to a step S6; if no, the process returns to the step S2.

S6: output the B-colored near infrared fluorescent signals.

S7: determine whether the phenomenon that a1 is not greater than a0 is owing to that the inspected area does not emit near infrared fluorescent signals; if yes, the process proceeds to a step S8; if no, decrease the intensity of the white light source, and the process returns to the step S2.

S8: output RGB colored video signals.

S9: output colored-fluorescent video signals according to the near infrared fluorescent video signals output in the step S6 and the RGB colored video signals output in the step S8.

It is preferred: a step S20 is interposed between the step S1 and the step S20. The step S20 is used to determine whether the excitation light source is turned on and has reached the maximum intensity; if yes, the process proceeds to the step S2; if no, adjust the excitation light source and determine whether the excitation light source has reached the maximum value. However, the step S20 is not necessarily used in other embodiments.

In one embodiment, determining whether the contrast of the near infrared fluorescent signal and the RGB background light achieves or approaches the predetermined best value in the step S5 further comprises steps:

S51: obtain an average of the intensities of the near infrared fluorescent signals within a given area of the blue light sensor, and denote the average as a1';

S52: determine whether the difference between a1' and a0 achieves or approaches a predetermined best value C; if yes, it is determined that the contrast of the near infrared fluorescent signals and the RGB background light has achieved or approached the predetermined best value; if no, it is determined that the contrast of the near infrared fluorescent signals and the RGB background light has not achieved or approached the predetermined best value yet.

The best value is determined beforehand to let the contrast of the fluorescent light and the colored background light achieve or approach the best state, whereby the fluorescent image can be clearly viewed in the colored-fluorescent image synthesized later. Naturally, the persons skilled in the art can use other ways to determine whether the contrast of the near infrared fluorescent light signal and the RGB background light achieves or approaches the predetermined best value. Any method able to determine whether the contrast of the near infrared fluorescent light signal and the RGB background light achieves or approaches the best predetermined value would be included by the scope of the present invention.

In one embodiment, determining whether the phenomenon that a1 is not greater than a0 is owing to that the inspected area does not emit near infrared fluorescent signals in the step S7 further comprises steps:

S71: determine whether a1 is smaller than a0; if no, decrease the intensity of the white light source, and the process returns to the step S2; if yes, decrease the intensity of the white light source, and the process proceeds to a step S72;

S72: determine in sequence whether an intensity a11, which is received by each pixel of the blue light sensor after the intensity of the white light source is decreased, is smaller than a0; if no, the process returns to the step S2; if yes, the process proceeds to a step S73;

S73: restore the intensity of the white light source to the value appearing before the intensity of the white light source is decreased;

S74: the red, green and blue light sensors respectively outputs their own light signals.

Naturally, the persons skilled in the art may use other methods to determine whether the phenomenon that a1 is not greater than a0 is owing to that the inspected area does not emit near infrared fluorescent signals. Any method able to determine whether the phenomenon that a1 is not greater than a0 is owing to that the inspected area does not emit near infrared fluorescent signals would be included by the scope of the present invention.

In another embodiment, the imaging method of a fluorescent image of the present invention may simultaneously adopt the abovementioned practical procedures to realize the step S5 and the abovementioned practical procedures to realize the step S7. In yet another embodiment, the imaging method of a fluorescent image of the present invention may adopt the abovementioned practical procedures to realize the step S5 and another method to realize the step S7. In still another embodiment, the imaging method of a fluorescent image of the present invention may adopt the abovementioned practical procedures to realize the step S7 and another method to realize the step S5.

Figure 3:
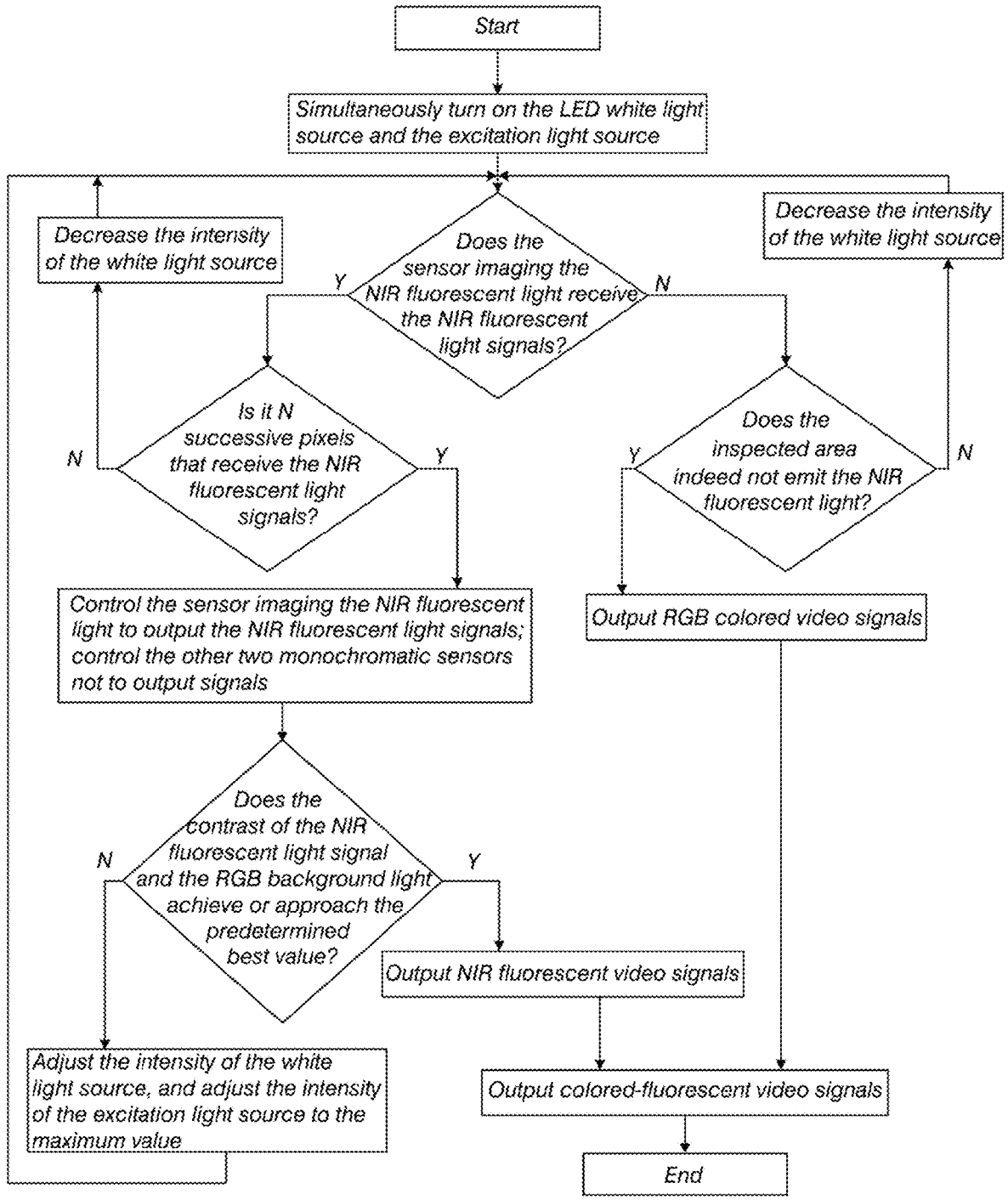
FIG. 3 is a flowchart schematically showing an imaging method of a fluorescent image according to yet another embodiment of the present invention.

Refer to FIG. 3. In another embodiment, the present invention also proposes an imaging method of a fluorescent image, which comprises the following steps.

S1: use a white light source and an excitation light source to illuminate an inspected area; respectively image the red light, green light and blue light of the reflection of the white light on a red light sensor, a green light sensor and a blue light sensor; use the blue light sensor to image the near infrared fluorescent light emitted from the inspected area.

The white light source may be a white LED light source or a light source synthesized with red, green and blue LED light sources. The excitation light source may be an 808±10 nm laser device used to excite the indocyanine green (ICG) agent of the inspected area to generate a near infrared fluorescent light. In this embodiment, each of the intensities of the white light source and the excitation light source may have an arbitrary value. In this embodiment, the blue light sensor is used to image the near infrared fluorescent light emitted from the inspected area. However, it should be understood: the present invention is not limited by this embodiment. In another embodiment, a red light sensor or a green light sensor is used to image the near infrared fluorescent light emitted from the inspected area.

S2: determine whether the blue light sensor receives the near infrared fluorescent signal; if yes, the process proceeds to a step S3; if no, the process proceeds to a step S6.

S3: determine whether the near infrared fluorescent light signal is received by N successive pixels; if yes, the process proceeds to a step S4; if no, decrease the intensity of the white light source, and the process returns to the step S2, wherein N is a natural number and N≥2.

S4: control the blue light sensor to output near infrared fluorescent signals, and assign a B color to the near infrared fluorescent signals; control the other two sensors not to output signals; determine whether the contrast of the near infrared fluorescent signal and the RGB background light achieves or approaches a predetermined best value; if yes, the process proceeds to a step S5; if no, increase or decrease the intensity of the white light source, and adjust the intensity of the excitation light source to the maximum value, and the process returns to the step S2.

S5: output near infrared fluorescent video signals.

S6: determine whether the phenomenon that the near infrared fluorescent signal is not received in the step S2 is owing to that the inspected area does not emit near infrared fluorescent signal; if yes, the process proceeds to a step S7; if no, decrease the intensity of the white light source, and the process returns to the step S2.

S7: output RGB colored video signals.

S8: output colored-fluorescent video signals according to the near infrared fluorescent video signals output in the step S5 and the RGB colored video signals output in the step S7.

In one embodiment, the step S2 includes steps:

S21: make weighted average of the intensities of the red light signals and the green light signals, which are received by each pixel of the red light sensor and the green light sensor, and multiply the weighted average by an experience coefficient r to obtain an intensity value (denoted by a0) of the blue light signal.

S22: determine in sequence whether an intensity a1 received by each pixel of the blue light sensor is greater than a0; if yes, determine that the blue light sensor receives the near infrared fluorescent signal; if no, determine that the blue light sensor does not receive the near infrared fluorescent signal.

Naturally, the persons skilled in the art may use other methods to determine whether the blue light sensor receives the near infrared fluorescent signal. Any method able to determine whether the blue light sensor receives the near infrared fluorescent signal would be included by the scope of the present invention.

In one embodiment, determining whether the contrast of the near infrared fluorescent signal and the RGB background light achieves or approaches the predetermined best value in the step S4 includes steps:

S41: acquire the average intensity (denoted by a1') of the near infrared fluorescent light signals within a given area;

S42: determine whether the difference between a1' and a0 achieves or approaches the predetermined best value; if yes, determine that the contrast of the near infrared fluorescent light signal and the RGB background light achieves or approaches the predetermined best value; if no, determine that the contrast of the near infrared fluorescent light signal and the RGB background light does not achieve or approach the predetermined best value.

Naturally, the persons skilled in the art may use other methods to determine whether the contrast of the near infrared fluorescent light signal and the RGB background light achieves or approaches the predetermined best value. Any method able to determine whether the contrast of the near infrared fluorescent light signal and the RGB background light achieves or approaches the predetermined best value would be included by the scope of the present invention.

In one embodiment, the step S6 includes steps:

S61: determine whether a1 is smaller than a0; if yes, decrease the intensity of the white light source, and the process returns to the Step S2; if no, decrease the intensity of the white light source, and the process proceeds to a step S62;

S62: determine in sequence whether the light intensity a11 received by each pixel of the sensor that images the near infrared fluorescent light is smaller than the light intensity a0 acquired in the step S21 after the intensity of the white light source is decreased; if no, the process returns to the step S2; if yes, the process proceeds to a step S63;

S63: restore the intensity of the white light source to the value appearing before the intensity of the white light source is decreased:

S64: the red light sensor, the green light sensor and the blue light sensor respectively output their light signals;

S65: output RGB colored video signals according to the light signals output by the red light sensor, the green light sensor and the blue light sensor.

Naturally, the persons skilled in the art may use other methods to determine whether the phenomenon that a1 is not greater than a0 is owing to that the inspected area does not emit near infrared fluorescent signals. Any method able to determine whether the phenomenon that a1 is not greater than a0 is owing to that the inspected area does not emit near infrared fluorescent signals would be included by the scope of the present invention.

In another embodiment, the imaging method of a fluorescent image of the present invention may simultaneously adopt the abovementioned practical procedures to realize the step S4 and the abovementioned practical procedures to realize the step S6. In yet another embodiment, the imaging method of a fluorescent image of the present invention may adopt the abovementioned practical procedures to realize the step S4 and another method to realize the step S6. In still another embodiment, the imaging method of a fluorescent image of the present invention may adopt the abovementioned practical procedures to realize the step S6 and another method to realize the step S4.

Figure 4:
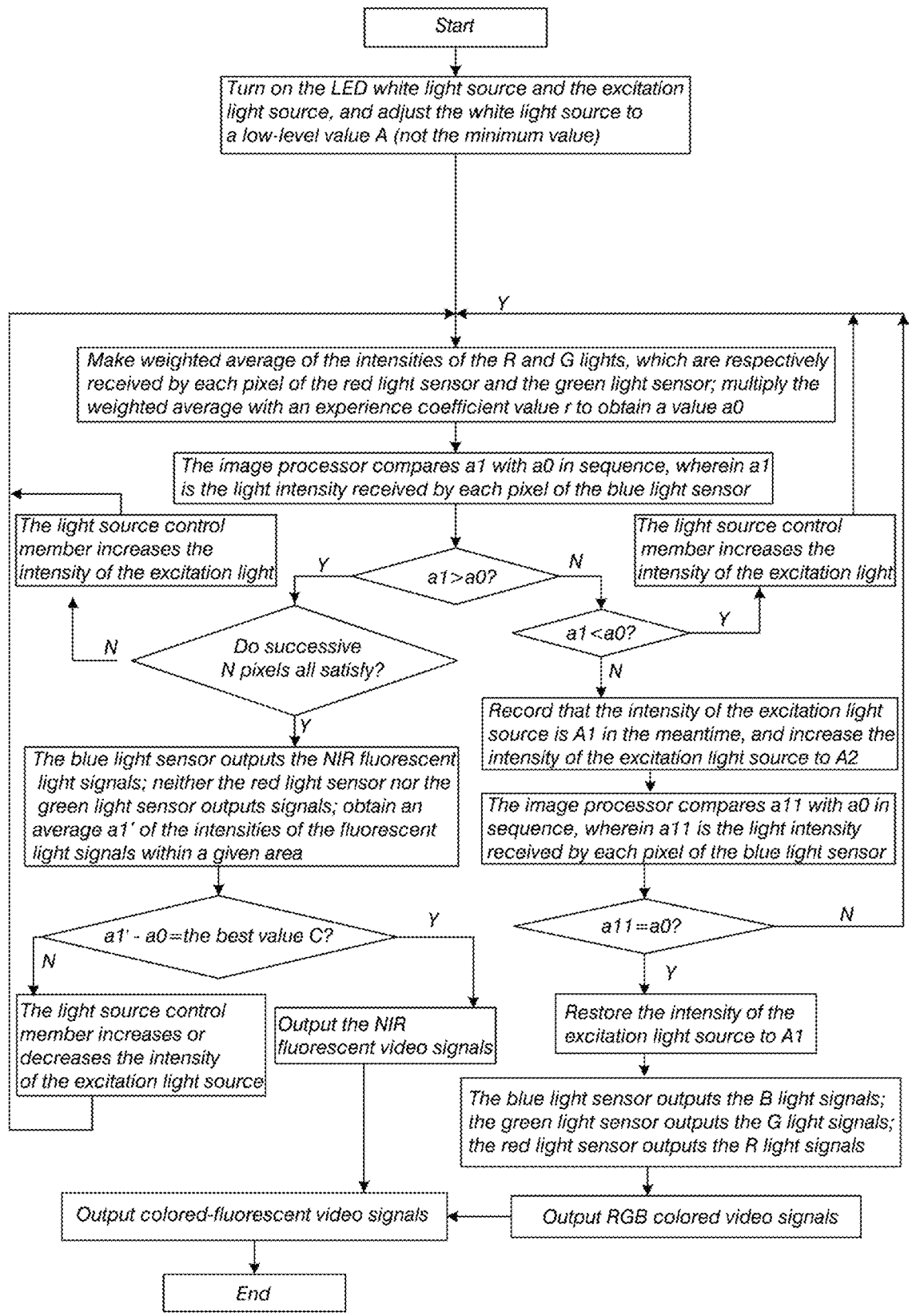
FIG. 4 is a flowchart schematically showing an imaging method of a fluorescent image according to still another embodiment of the present invention.

Refer to FIG. 4. In one embodiment, the intensity of the white light source is lowered (adjusted) to a value, which is A % (such as 30%) of the maximum value, wherein the intensity of the white light source should be a value as small as possible but must be greater than noise; the intensity of the excitation light may be an arbitrary value within a range from zero to maximum. In the succeeding process, only the intensity of the excitation light source is adjusted to make the contrast of the near infrared fluorescent light and the RGB light achieve or approach the best value.

In the embodiment shown in FIG. 4, the imaging method of a fluorescent image of the present invention performs image processing before generating the colored-fluorescent images, comprising steps: respectively imaging the red, green and blue lights of the white light on three monochromatic sensors under the precondition that the software processing speed is not affected; imaging the near infrared fluorescent light on one of the monochromatic sensors; determining whether the sensor used to receive the near infrared fluorescent light receives the fluorescent signal; calculating the light intensity received by the sensor receiving the fluorescent signal and the light intensities received by the other two sensors; automatically adjusting the projection intensity of the white light source and/or the excitation light source according to the difference of the intensities of the two types of light signals, whereby a closed-loop system is formed to simultaneously present the colored and florescent images on a picture with the best contrast. The method of the present invention can automatically adjust the intensities of the white light and the excitation light to maintain a given difference between the fluorescent light signal and the background colored light signal. Therefore, the method of the present invention can precisely and conveniently determine whether the fluorescent light signal exists. While the fluorescent light signal exists, the method of the present invention guarantees that the brightness of the colored background is sufficient to allow physicians to observe the body cavity conveniently and precisely. Because of performing image processing before forming images, the method of the present invention handles smaller volume of data, computes faster, and output pictures smoothly.

Figure 5:
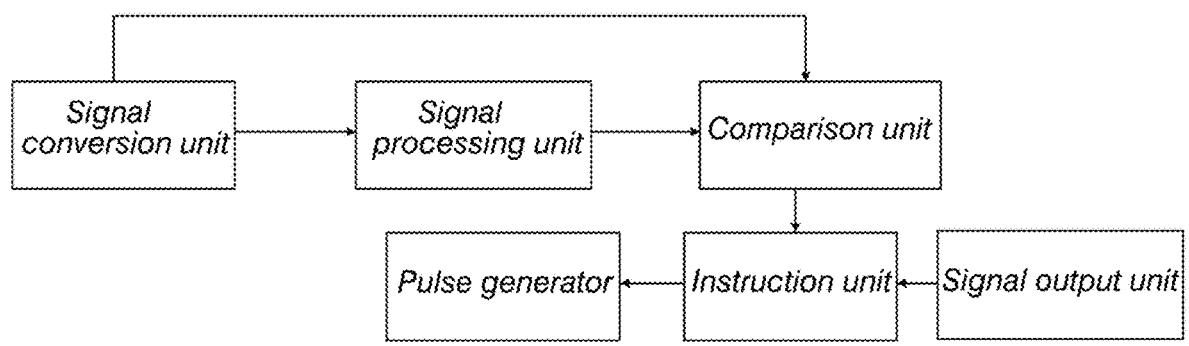
FIG. 5 is a block diagram schematically showing an image processing system according to one embodiment of the present invention.

Refer to FIG. 5. The present invention also proposes an image processing system, which comprises a pulse generator and an image processor. The image processor further comprises a signal conversion unit, a signal processing unit, a comparison unit, an instruction unit, and a signal output unit.

The signal conversion unit respectively picks up the intensity values of the light signals received by each pixel of the red light sensor, the green light sensor and the blue light sensor and undertakes the photoelectric conversions of the light signals. The red light sensor, the green light sensor and the blue light sensor respectively image the red light, the green light and the blue light of the reflection of the white light. The blue light sensor images the near infrared fluorescent light. The reflection of the white light is reflected from an inspected area illuminated by a white light source. The near infrared fluorescent light is emitted from the inspected area illuminated by an excitation light source. The white light source may be a white LED light source or a light source synthesized with red, green and blue LED light sources. The excitation light source may be an 808±10 nm laser device used to excite the indocyanine green (ICG) agent of the inspected area to generate a near infrared fluorescent light. In this embodiment, the blue light sensor is used to image the near infrared fluorescent light emitted from the inspected area. However, the present invention is not limited by this embodiment. In another embodiment, a red light sensor or a green light sensor is used to image the near infrared fluorescent light emitted from the inspected area.

The signal processing unit makes weighted average of the intensity values of the light signals, which are received by each pixel of the red and green light sensors. The weighted average is multiplied by an experience coefficient r to obtain an intensity value (denoted by a0) of the blue light signal.

The comparison unit compares an intensity value a1 with the intensity value a0, wherein a photoelectric conversion of the light signal received by each pixel of the blue light sensor is undertaken to obtain the intensity value a1.

The instruction unit receives the comparison result from the comparison unit to make determinations and perform corresponding operations.

In the case that a1>a0, if N successive pixels all satisfy a1>a0, the instruction unit sends out a first instruction to the pulse generator; the pulse generator controls the blue light sensor to output the near infrared fluorescent signal and controls the other two sensors not to output light signals. Let a1' be the average value of the intensities of the near infrared fluorescent light signals within a given area of the blue light sensor. If the difference between a1' and a0 achieves or approaches a predetermined best value, the instruction unit sends out a second instruction. If the difference between a1' and a0 does not achieve or approach the predetermined best value, the instruction unit sends out a third instruction to decrease the intensity of the white light source.

In the case that a1>a0, if N successive pixels do not all satisfy a1>a0, the instruction unit sends out the third instruction to decrease the intensity of the white light source. If the difference between a1' and a0 does not achieve or approach the predetermined best value, the instruction unit sends out a fourth instruction to increase or decrease the intensity of the white light source.

In the case that a1<a0, the instruction unit sends out the third instruction to decrease the intensity of the white light source.

In the case that a1=a0, the instruction unit sends out the third instruction to decrease the intensity of the white light source, and compare an intensity value a11 with the intensity value a0, wherein the photoelectric conversion of the light signal received by each pixel of the blue light sensor is undertaken after decreasing the intensity of the white light source to obtain the intensity value a11. If a11<a0, the instruction unit sends out a fifth instruction to restore the intensity of the white light source to the value appearing before the intensity of the white light source is decreased, and sends out the second instruction to the pulse generator to control the red, green and blue sensors to respectively output the red, green and blue light signals under the condition that the intensity of the white light source has been restored.

The signal output unit receives the second instruction and outputs the colored-fluorescent video signals according to the near infrared fluorescent signal output by the near infrared fluorescent light sensor and the red, green and blue light signals output by the red light, green light and blue light sensors.

Figure 6:
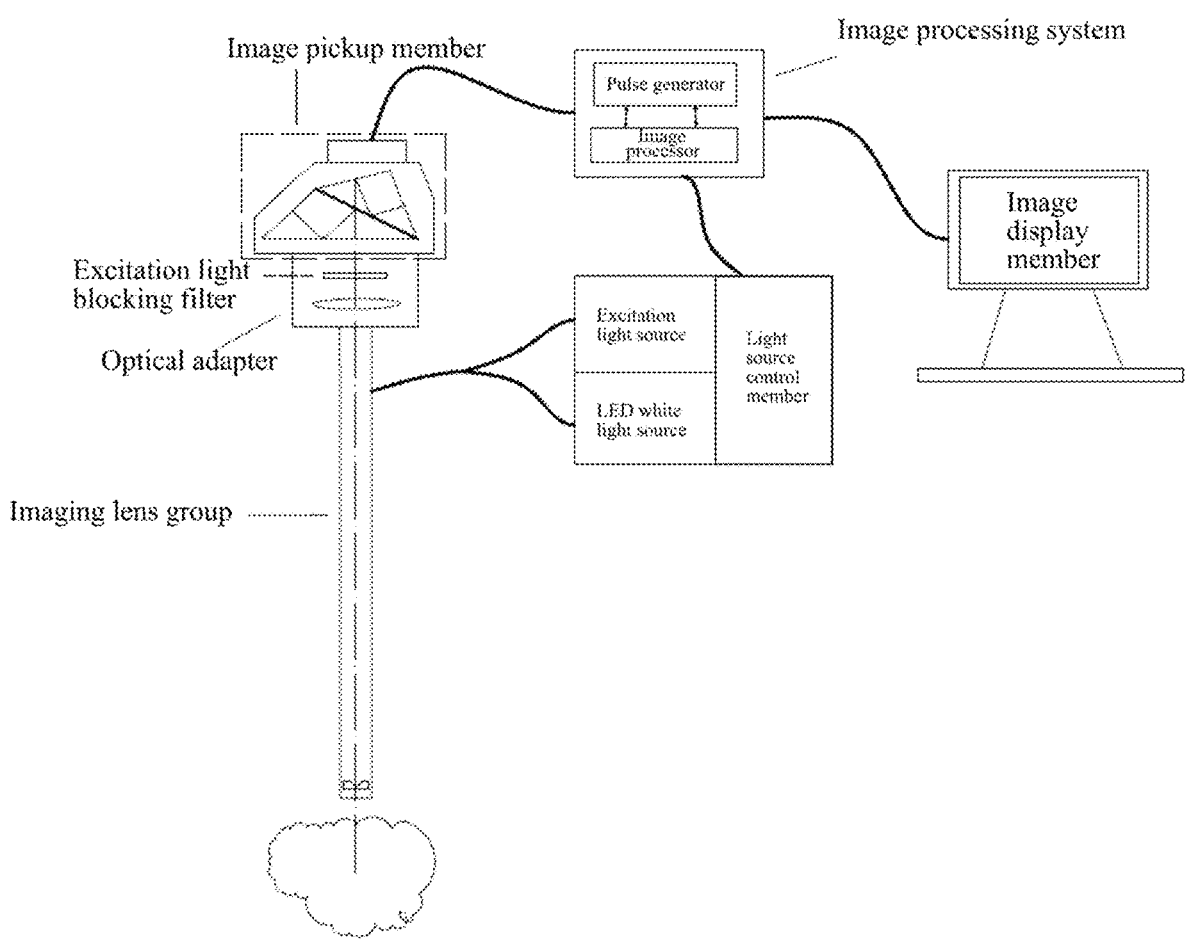
FIG. 6 is a diagram schematically showing a fluorescent endoscope illuminating and imaging device according to one embodiment of the present invention.

Refer to FIG. 6. The present invention also proposes a fluorescent endoscope illuminating and imaging device. In one embodiment, the fluorescent endoscope illuminating and imaging device of the present invention comprises a light projection device, an optical pickup member, an image pickup member, an image processing system, and an image display member.

The light projection device provides a white light and an excitation light whose intensities are adjustable to illuminate an inspected area. The white light source may be a white LED light source or a light source synthesized with red, green and blue LED light sources. The excitation light source may be an 808±10 nm laser device used to excite the indocyanine green (ICG) agent of the inspected area to generate a near infrared fluorescent light. In details, the light projection device includes a white light source, an excitation light source and a light source control member. The light source control member is used to adjust the intensities of the white light source and the excitation light source.

Figure 7:
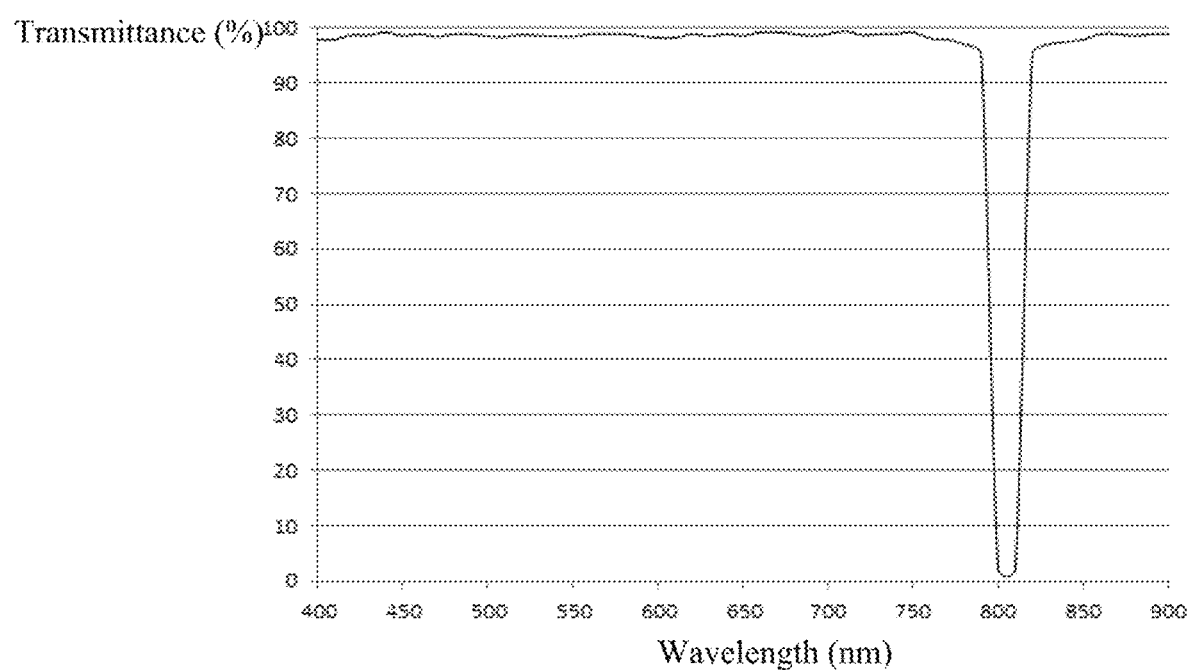
FIG. 7 is a diagram showing a surface coating curve of a filter able to block an excitation light according to one embodiment of the present invention.

The optical pickup member transmits and couples the white light reflected from the inspected area and the near infrared fluorescent light emitted from the inspected area to the image pickup member. In details, the optical pickup member includes an imaging lens group and an optical adapter. The optical adapter is disposed at the rear end of the imaging lens group. The imaging lens group transmits the white light reflected from the inspected area and the near infrared fluorescent light emitted from the inspected area. The optical adapter couples the reflection of the white light and the emitted near infrared fluorescent light to the image pickup member. The imaging lens group is a group of optical lenses, able to image multiple spectra of lights, including visible light and near infrared fluorescent light. The optical adapter includes filters, which screen out the excitation light emitted from the inspected area and allow the reflection of the white light and the near infrared fluorescent light to pass. FIG. 7 shows the surface coating curve of the filter. It is learned from FIG. 7: the filter allows the visible light having a wavelength of 400-800 nm and the near infrared fluorescent light having a wavelength of 830-850 nm to pass and blocks the excitation light having a wavelength of 808 nm.

In a preferred embodiment, the imaging lens group is a portion of the endoscope, whereby the entire system has a compact structure. Thus, the endoscope using the present invention may replace the existing endoscope without interfering with the operation of physicians.

Figure 8:
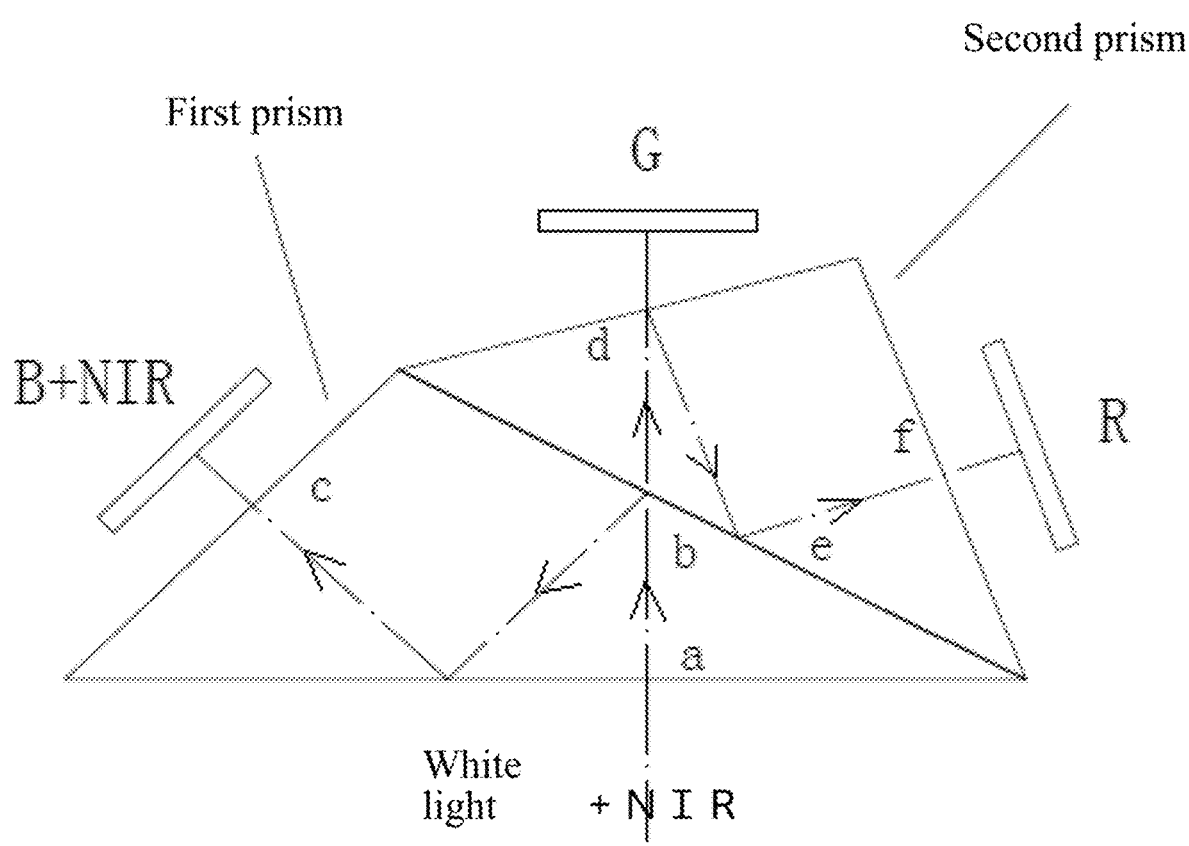
FIG. 8 is a diagram schematically showing internal optical paths of a light-splitting prism group according to one embodiment of the present invention.

The image pickup member includes a light-splitting prism group, a red light sensor, a green light sensor and a blue light sensor. The light-splitting prism group includes two prisms. The light-splitting prism group is disposed in the rear end of the optical adapter. The light-splitting prism group splits the reflection of the white light into an R light, a G light, and a B light, which are separately distributed in three channels, and respectively images the R, G and B lights on the red light sensor, the green light sensor and the blue light sensor. The NIR fluorescent light is allocated to the channel of the B light. The NIR fluorescent light, together with the B light, is imaged on the blue light sensor, as shown in FIG. 8. In details, the white light and the near infrared fluorescent light, which are incident to the light-splitting prism group, are divided into two parts: the R+G lights and the B+NIR lights. The R+G lights pass through a face b of a first prism. The G light further passes through a face d of a second prism and then is imaged on the green light sensor. The R light is reflected by the face d of the second prism, next totally reflected to pass through a face f of the second prism, and then imaged on the red light sensor. The B+NIR lights are reflected by the face b of the first prism, next totally reflected to pass through a face c of the first prism, and then imaged on the blue light sensor.

Figure 9:
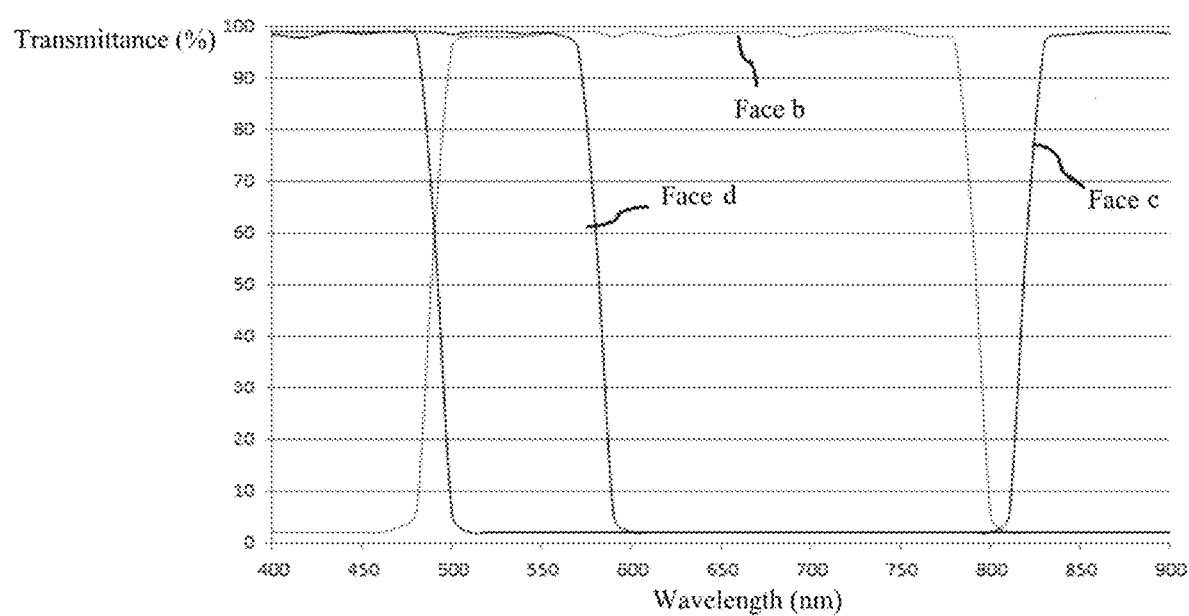
FIG. 9 is a diagram showing coating curves of different faces of a light-splitting prism group according to one embodiment of the present invention.

FIG. 9 shows the coating curves of the faces b and c of the first prism and the face d of the second prism. The coating of the face b is characterized in allowing the green light and the red light to pass and reflecting the blue light and the NIR fluorescent light. The coating of the face c is characterized in allowing the blue light and the NIR fluorescent light to pass and blocking the green light and the red light. The coating of the face d is characterized in allowing the green light to pass and reflecting the red light. Because the blue light is dimmer, it contributes less in presenting the tissue of human bodies. Therefore, the near infrared fluorescent light is allocated to the channel of the B light and imaged on the blue light sensor. In other words, the NIR fluorescent light and the B light share the blue light sensor. However, the present invention is not limited by this embodiment. In other embodiments, the red light sensor or the green light sensor may be used to treat and image the near infrared fluorescent light emitted from the inspected area.

The image processing system further comprises a pulse generator and an image processor. The image processor includes a signal conversion unit, a signal processing unit, a comparison unit, an instruction unit, and a signal output unit.

The signal conversion unit respectively picks up the intensity values of the light signals received by each pixel of the red light sensor, the green light sensor and the blue light sensor and undertakes the photoelectric conversions of the light signals.

The signal processing unit makes weighted average of the intensity values of the light signals, which are received by each pixel of the red and green light sensors. The weighted average is multiplied by an experience coefficient r to obtain an intensity value (denoted by a0) of the blue light signal.

The comparison unit compares an intensity value a1 with the intensity value a0, wherein a photoelectric conversion of the light signal received by each pixel of the blue light sensor is undertaken to obtain the intensity value a1.

The instruction unit receives the comparison result from the comparison unit to make determinations and perform corresponding operations.

In the case that a1>a0, if N successive pixels all satisfy a1>a0, the instruction unit sends out a first instruction to the pulse generator; the pulse generator controls the blue light sensor to output the near infrared fluorescent signal and controls the other two sensors not to output light signals. In other words, the pulse generator closes the output channels of the red light sensor and the green light sensor so that the red light sensor and the green light sensor would not output signals. Let a1' be the average value of the intensities of the near infrared fluorescent light signals within a given area of the blue light sensor. If the difference between a1' and a0 achieves or approaches a predetermined best value, the instruction unit sends out a second instruction. If the difference between a1' and a0 does not achieve or approach the predetermined best value, the instruction unit sends out a third instruction to decrease the intensity of the white light source.

In the case that a1>a0, if N successive pixels do not all satisfy a1>a0, the instruction unit sends out the third instruction to decrease the intensity of the white light source. If the difference between a1' and a0 does not achieve or approach the predetermined best value, the instruction unit sends out a fourth instruction to increase or decrease the intensity of the white light source.

In the case that a1<a0, the instruction unit sends out the third instruction to decrease the intensity of the white light source.

In the case that a1=a0, the instruction unit sends out the third instruction to decrease the intensity of the white light source, and compare an intensity value a11 with the intensity value a0, wherein the photoelectric conversion of the light signal received by each pixel of the blue light sensor is undertaken after decreasing the intensity of the white light source to obtain the intensity value a11. If a11<a0, the instruction unit sends out a fifth instruction to restore the intensity of the white light source to the value appearing before the intensity of the white light is decreased, and sends out the second instruction to the pulse generator to control the red, green and blue sensors to respectively output the red, green and blue light signals under the condition that the intensity of the white light source has been restored. In other words, the pulse generator opens the output channels of the red light sensor and the green light sensor so that the red light sensor and the green light sensor output corresponding light signals.

The signal output unit receives the second instruction and outputs the colored-fluorescent video signals according to the near infrared fluorescent signal output by the near infrared fluorescent light sensor and the red, green and blue light signals output by the red light, green light and blue light sensors. In other words, the white light reflected from the normal tissue of the inspected area is processed and synthesized to output the RGB colored signal; the near infrared fluorescent light emitted from the abnormal tissue of the inspected area is output as the B color.

The image display member includes a display device, undertaking signal conversion of the colored-fluorescent video signals output by the image processing system, and outputting colored-fluorescent images on the display device.

Below, an embodiment is used to show an application of the fluorescent endoscope illuminating and imaging device of the present invention.

Firstly, inject an ICG agent into a human body. After a period of time, turn on the white light source and the laser light source simultaneously, and adjust the white light source to an intensity A1 and the laser light source to the maximum intensity. Thus, the surface of the tissue reflect the white light and the excitation light and emits the near infrared fluorescent light. The reflected and emitted lights enter the imaging lens group (such as a laparoscope), pass through the optical adapter, and reach the front end of the light-splitting prism group. The excitation light is screened out by the filter inside the optical adapter. The white light and the near infrared fluorescent light reach the light-splitting prism group, passing through the face a of the first prism to enter the first prism. The face b of the first prism allows the R light and the G light of the white light to enter the second prism and reflects the B light and the NIR fluorescent light to the face a of the first prism. The B light and the NIR fluorescent light are totally reflected by the face a of the first prism, go out of the first prism from the face c of the first prism, and then form images on the blue light sensor. After entering the second prism, the R light and the G light reach the face d of the second prism. The G light goes out of the second prism from the face d and then forms images on the green light sensor. The R light is reflected to the face e of the second prism, totally reflected by the face e, going out of the second prism from the face f of the second prism, and then forming images on the red light sensor.

The image processing system processes the generated R, G, B and NIR fluorescent light signals. The image processing system makes weighted average of the intensities of the R and G light signals and multiplies the weighted average with an experience coefficient r to obtain a result a0. While the light signal intensity a1 is greater than a0, a B-colored NIR fluorescent light signal is output, wherein a1 is the light signal intensity detected by the blue light sensor. In the meantime, the green light sensor does not output signals, and the red light sensor does not output signals either. Alternatively, together with the outputting of the B light, the red light sensor and the green light sensor respectively output the R light and the G light. Next, RGB colored signals are output. Then, the colored-fluorescent video signals are output.

While the blue light sensor has detected all the NIR fluorescent light signals, the image processor outputs an instruction to the light source control member. The light source control member gradually increases or decreases the intensity of the LED white light source to make the difference between a1' (the averaged intensity of the fluorescent light signals) and a0 achieve or approach the best value C. In other words, the contrast of the fluorescent light and the colored background light reaches the best state.

Then, the colored-fluorescent video signals are output to the image display member. The display device converts the colored-fluorescent video signals and presents the colored-fluorescent images on the screen, wherein the fluorescent light is presented as the blue color, and the background is colored.

The persons skilled in the art may make modifications and variations of the present invention without departing from the spirit and scope of the present invention. Therefore, any equivalent modification or variation according to the spirit or claims of the present invention is to be also included by the scope of the present invention.

What is claimed is:

1. A method of forming a fluorescent image, comprising steps:

S1: illuminating an inspected area with using a white light source and an excitation light source, wherein said excitation light source is adjusted to have a highest intensity; respectively imaging a red light, a green light and a blue light of a reflection of a white light on a red light sensor, a green light sensor and a blue light sensor; using one of said red light sensor, said green light sensor and said blue light sensor to image a near infrared fluorescent light emitted from said inspected area;

S2: with an image processor, making a weighted average of intensities of light signals of two of said red light, said green light and said blue light, which are received by each pixel of two said sensors not receiving said near infrared fluorescent light, to obtain an intensity a0 of a third light signal;

S3: with the image processor, determining in sequence whether an intensity a1, which is received by each pixel of said sensor imaging said near infrared fluorescent light, is greater than said intensity value a0 generated in said step S2; if yes, proceeding to a step S4; if no, proceeding to a step S8;

S4: with the image processor, determining whether successive N pixels all satisfy a1>a0; if yes, proceeding to a step S5; if no, lowering an intensity of said white light source, and returning to said step S2, wherein N is a natural number and N>2;

S5: controlling said sensor imaging said near infrared fluorescent light, to output near infrared fluorescent light signals, and controlling the other two said sensors not to output signals; acquiring an average intensity a1' of said near infrared fluorescent light signals within a given area of a corresponding said sensor;

S6: with the image processor, determining whether a difference between a1' and a0 achieves a predetermined best value; if yes, proceeding to a step S7; if no, adjusting said intensity of said white light source, and returning to said step S2;

S7: outputting near infrared fluorescent video signals;

S8: with the image processor, determining whether a1<a0; if yes, decreasing said intensity of said white light source, and returning to said step S2; if no, proceeding to a step S9;

S9: decreasing said intensity of said white light source;

S10: with the image processor, determining in sequence whether an intensity a1 received by the pixels of said sensor imaging said near infrared fluorescent light is smaller than said light intensity a0 acquired in said step S2 after said intensity of said white light source is decreased; if no, returning to said step S2; if yes, proceeding to a step S11;

S11: restoring said intensity of said white light source to a value of said intensity of said white light source used before said intensity of said white light source is decreased;

S12: outputting RGB colored video signals;

S13: outputting colored-fluorescent video signals according to said near infrared fluorescent video signals output in said step S7 and said RGB colored video signals output in said step S12.

2. The method of forming a fluorescent image according to claim 1, wherein a step S20 is interposed between said step S1 and said step S2, wherein said step S20: determining whether said excitation light source is turned on and has reached a maximum intensity; if yes, proceeding to said step S2; if no, adjusting said excitation light source and determining whether said excitation light source has reached said maximum intensity.

3. A method of forming a fluorescent image, comprising steps:

S1: illuminating the inspected area with using a white light source and an excitation light source; respectively imaging a red light, a green light and a blue light of a reflection of a white light on a red light sensor, a green light sensor and a blue light sensor; using one of said red light sensor, said green light sensor and said blue light sensor to image a near infrared fluorescent light emitted from said inspected area;

S2: with an image processor, determining whether said sensor imaging said near infrared fluorescent light, receives near infrared fluorescent light signals; if yes, proceeding to a step S3; if no, proceeding to a step S6;

S3: with an image processor, determining whether said near infrared fluorescent light signals are received by N successive pixels; if yes, proceeding to a step S4; if no, decreasing an intensity of said white light source, and returning to said step S2, wherein N is a natural number and N≥2;

S4: controlling said sensor imaging said near infrared fluorescent light, to output near infrared fluorescent light signals, and controlling the other two said sensors not to output signals; determining whether a contrast of said near infrared fluorescent light signal and an RGB background light achieves a predetermined value; if yes, proceeding to a step S5; if no, adjusting said intensity of said white light source, or adjusting an intensity of said excitation light source, or adjusting said intensity of said white light source and said intensity of said excitation light source at the same time, and then returning to said step S2;

S5: outputting near infrared fluorescent video signals;

S6: with an image processor, determining whether a reason why said near infrared fluorescent light signals are not received in said step S2 is that said inspected area does not emit said near infrared fluorescent light; if yes, proceeding to a step S7; if no, decreasing said intensity of said white light source, and returning to the step S2;

S7: outputting RGB colored video signals;

S8: outputting colored-fluorescent video signals according to said near infrared fluorescent video signals output in said step S5 and said RGB colored video signals output in said step S7.

4. The method of forming a fluorescent image according to claim 3, wherein said step S2 further comprises S21: with an image processor, making a weighted average of intensities of light signals of two of said red light, said green light and said blue light, which are received by each pixel of two said sensors not receiving said near infrared fluorescent light, to obtain an intensity value a0 of a third light signal;

S22: with an image processor, determining in sequence whether a light intensity a1 received by the pixels of said sensor imaging said near infrared fluorescent light is greater than said intensity value a0 generated in said step S21; if yes, determining that said sensor, imaging said near infrared fluorescent light, receives said near infrared fluorescent signals; if no, determining that said sensor, imaging said near infrared fluorescent light, does not receive said near infrared fluorescent signals.

5. The method of forming a fluorescent image according to claim 4, wherein determining whether said contrast of said near infrared fluorescent light signal and said RGB background light achieves said predetermined value in said step S4 further comprises
- S41: acquiring an average intensity a1' of said near infrared fluorescent light signals within a given area;
- S42: with an image processor, determining whether a difference between a1' and a0 achieves a predetermined value; if yes, determining that said contrast of said near infrared fluorescent light signal and said RGB background light achieves said predetermined value; if no, determining that said contrast of said near infrared fluorescent light signal and said RGB background light does not achieve said predetermined value.

6. The method of forming a fluorescent image according to claim 4, wherein said step S6 further comprises
- S61: with an image processor, determining whether a1 is smaller than a0; if yes, decreasing said intensity of said white light source, and returning to said Step S2; if no, decreasing said intensity of said white light source, and proceeding to a step S62;
- S62: with an image processor, determining in sequence whether a light intensity all received by the pixels of said sensor imaging said near infrared fluorescent light is smaller than said light intensity a0 acquired in said step S21; if no, returning to the step S2; if yes, proceeding to a step S63;
- S63: restoring said intensity of said white light source to a value of said intensity of said white light source used previously in said step S61 and proceeding to said step S62;
- S64: said red light sensor, said green light sensor and said blue light sensor respectively outputting their light signals;
- S65: outputting said RGB colored video signals according to light signals output by said red light sensor, said green light sensor and said blue light sensor.

7. The method of forming a fluorescent image according to claim 3, wherein adjusting said intensity of said excitation light source in said step S4 is to adjust said intensity of said excitation light source to a maximum value.

8. An image processing system, comprising a pulse generator and an image processor, wherein said image processor includes:
- a signal conversion processor, respectively receiving intensity values of light signals received by each pixel of a red light sensor, a green light sensor and a blue light sensor, and undertaking photoelectric conversions of said light signals, wherein said red light sensor, said green light sensor and said blue light sensor respectively image a red light, a green light and a blue light of a reflection of a white light; one of said red light sensor, said green light sensor and said blue light sensor images a near infrared fluorescent light; said reflection of the white light is reflected from an inspected area illuminated by a white light source; said near infrared fluorescent light is emitted from said inspected area illuminated by an excitation light source;
- a signal processing processor, making a weighted average of said intensity values of light signals, which are generated by said photoelectric conversions, of two of said red light, said green light and said blue light, which are received by each pixel of two said sensors not receiving said near infrared fluorescent light, to obtain an intensity value a0 of a third light signal;
- a comparison processor, comparing an intensity value a1 with said intensity value a0, wherein a photoelectric conversion of light signals received by the pixels of said sensor receiving said near infrared fluorescent light is undertaken to obtain said intensity value a1;
- an instruction processor, receiving a comparison result from said comparison processor to make a determination and perform a corresponding operation, wherein in a case that a1>a0, if N successive pixels all satisfy a1>a0, said instruction processor sends out a first instruction to said pulse generator; said pulse generator controls said sensor, receiving said near infrared fluorescent light, to output near infrared fluorescent light signals and controls the other two said sensors not to output light signals; let a1' be an average value of intensities of said near infrared fluorescent light signals within a given area of said sensor receiving said near infrared fluorescent light; if a difference between a1' and a0 achieves a predetermined value, said instruction processor sends out a second instruction; if a difference between a1' and a0 does not achieve said predetermined value, said instruction processor sends out a third instruction to decrease an intensity of said white light source;

in said case that a1>a0, if N successive pixels do not all satisfy a1>a0, said instruction processor sends out said third instruction to decrease said intensity of said white light source; if a difference between a1' and a0 does not achieve said predetermined value, said instruction processor sends out a fourth instruction to increase or decrease said intensity of said white light source;

in a case that a1<a0, said instruction processor sends out said third instruction to decrease said intensity of said white light source;

in a case that a1=a0, said instruction processor sends out said third instruction to decrease said intensity of said white light source, and compare an intensity value all with said intensity value a0, wherein the photoelectric conversion of light signals received by the pixels of said sensor receiving said near infrared fluorescent light is undertaken after decreasing said intensity of said white light source to obtain said intensity value all; if all1<a0, said instruction processor sends out a fifth instruction to restore said intensity of said white light source to a value of said intensity of said white light used before said intensity of said white light is decreased, and sends out said second instruction to said pulse generator to control said red light sensor, said green light sensor and said blue light sensor to respectively output a red light signal, a green light signal and a blue light signal under a condition that said intensity of said white light source has been restored;

a signal output processor, receiving said second instruction and outputting colored-fluorescent video signals according to said near infrared fluorescent signal output by said sensor receiving said near infrared fluorescent light, said red light signal, said green light signal and said blue light signal output by said red light sensor, said green light sensor and said blue light sensor.

9. A fluorescent endoscope illuminating and imaging device, comprising the image processing system according to claim 8.

10. The fluorescent endoscope illuminating and imaging device according to claim 9, further comprising a light projection processor, an optical pickup member, an image pickup member, and an image display member, wherein
said light projection processor provides said white light and an excitation light whose intensities are adjustable to illuminate an inspected area;

said optical pickup member transmits and couples said white light reflected from said inspected area and said near infrared fluorescent light emitted from said inspected area to said image pickup member;

said image pickup member includes a light-splitting prism group, said red light sensor, said green light sensor and said blue light sensor; said light-splitting prism group splits the white light, which is reflected from said inspected area and coupled to said image pickup member, into the red light, the green light, and the blue light, and respectively images said red light, said green light, and said blue light on said red light sensor, said green light sensor and said blue light sensor; said near infrared fluorescent light, which is coupled to said image pickup member and passes through said light-splitting prism group, is imaged on one of said red light sensor, said green light sensor and said blue light sensor;

said image display member undertakes a signal conversion of said colored-fluorescent video signals output by said image processing system and outputs colored-fluorescent images.

11. The fluorescent endoscope illuminating and imaging device according to claim 10, wherein said light projection processor includes said white light source, said excitation light source and a light source controller, wherein said light source controller is used to modify intensities of said white light source and said excitation light source.

12. The fluorescent endoscope illuminating and imaging device according to claim 10, wherein said optical pickup member includes an imaging lens group and an optical adapter, wherein said optical adapter is disposed at a rear end of said imaging lens group; said imaging lens group transmits said white light reflected from said inspected area and said near infrared fluorescent light emitted from said inspected area; said optical adapter couples said white light reflected from said inspected area and said near infrared fluorescent light emitted from said inspected area to said image pickup member.

13. The fluorescent endoscope illuminating and imaging device according to claim 12, wherein said optical adapter includes light filters; said light filters screens out said excitation light from said inspected area and allows said white light reflected from said inspected area and said near infrared fluorescent light emitted from said inspected area to pass.

14. The fluorescent endoscope illuminating and imaging device according to claim 12, wherein said imaging lens group is a portion of said a fluorescent endoscope.

15. The method of forming a fluorescent image according to claim 5, wherein said step S6 further comprises:
S61: determining whether a1 is smaller than a0; if yes, decreasing said intensity of said white light source, and returning to said Step S2; if no, decreasing said intensity of said white light source, and proceeding to a step S62;
S62: determining in sequence whether a light intensity all received by the pixels of said sensor imaging said near infrared fluorescent light is smaller than said light intensity a0 acquired in said step S21; if no, returning to the step S2; if yes, proceeding to a step S63;
S63: restoring said intensity of said white light source to a value of said intensity of said white light source used previously in said step S61 and proceeding to said step S62;
S64: said red light sensor, said green light sensor and said blue light sensor respectively outputting their light signals;
S65: outputting said RGB colored video signals according to light signals output by said red light sensor, said green light sensor and said blue light sensor.

16. The fluorescent endoscope illuminating and imaging device according to claim 11, wherein said optical pickup member includes an imaging lens group and an optical adapter, wherein said optical adapter is disposed at a rear end of said imaging lens group; said imaging lens group transmits said white light reflected from said inspected area and said near infrared fluorescent light emitted from said inspected area; said optical adapter couples said white light reflected from said inspected area and said near infrared fluorescent light emitted from said inspected area to said image pickup member.

* * * * *